US00PP28695P3

(12) United States Plant Patent
Wood

(10) Patent No.: US PP28,695 P3
(45) Date of Patent: Nov. 28, 2017

(54) ***PHYSOCARPUS* PLANT NAMED 'SMNPOBLR'**

(50) Latin Name: *Physocarpus opulifolius*
Varietal Denomination: SMNPOBLR

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 57 days.

(21) Appl. No.: 14/756,874

(22) Filed: Oct. 21, 2015

(65) Prior Publication Data

US 2017/0118892 P1 Apr. 27, 2017

(51) Int. Cl.
*A01H 5/02* (2006.01)

(52) U.S. Cl.
USPC ..... Plt./226

(58) Field of Classification Search
USPC ..... Plt./226
See application file for complete search history.

(56) References Cited

U.S. PATENT DOCUMENTS

PP16,371 P2 * 3/2006 Davasse ..... Plt./226

OTHER PUBLICATIONS

Spring Meadow Nursery, Inc. Flowering Shrubs Starter Plants Catalog and Shrub Reference 2015-2016, retrieved on Feb. 13, 2017, retrieved from the Internet at <http://springmeadownursery.com/content-media/catalog_2015.pdf> pp. 1-6, 24 and 77.*

* cited by examiner

*Primary Examiner* — June Hwu
(74) *Attorney, Agent, or Firm* — Cassandra Bright

(57) ABSTRACT

A new and distinct *Physocarpus* cultivar named 'SMNPOBLR' is disclosed, characterized by a good mildew resistance, bright red stems, white flowers, lightly flushed pink that age to bright red seed capsules, and very strong red/orange spring leaf flush that turn to dark maroon for the summer. The new variety is a *Physocarpus*, normally produced as an outdoor garden or container plant.

3 Drawing Sheets

Latin name of the genus and species: *Physocarpus opulifolius.*

Variety denomination: 'SMNPOBLR'.

BACKGROUND OF THE INVENTION

The new *Physocarpus* cultivar is a product of a planned breeding program conducted by the inventor, Timothy D. Wood, in Grand Haven, Minn. The objective of the breeding program was to produce new *Physocarpus* varieties with unique foliage and powdery mildew resistance. The open pollination resulting in this new variety was made during Summer of 2010.

The new *Physocarpus* 'SMNPOBLR' resulted from an open pollination with *Physocarpus opulifolius* 'Center Glow' U.S. Plant Pat. No. 16,894 as the seed parent. The pollen parent is unknown. The new variety was identified as a potentially interesting selection in Summer 2013, at a nursery in Grand Haven, Minn.

Asexual reproduction of the new cultivar 'SMNPOBLR' by softwood cuttings was first performed during Summer of 2013, at commercial greenhouse in Grand Haven, Minn. Subsequent propagation has shown that the unique features of this cultivar are stable and reproduced true to type in 5 successive generations.

SUMMARY OF THE INVENTION

The cultivar 'SMNPOBLR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNPOBLR' These characteristics in combination distinguish 'SMNPOBLR' as a new and distinct *Physocarpus* cultivar:

1. Bright red stems
2. New foliage has a very strong red/orange Spring leaf flush, turning dark maroon during Summer.
3. Good mildew resistance.
4. White to light pink flowers that age to bright red seed capsules

PARENT COMPARISON

Plants of the new cultivar 'SMNPOBLR' are similar to plants of the seed parent in most horticultural characteristics, however, plants of the new cultivar 'SMNPOBLR' differ in the following:

1. Foliage of the new variety has a red/orange Spring flush. The seed parent variety has a Spring flush coloration of lime green to yellow with orange-maroon.
2. The new variety has resistance to powdery mildew, the seed parent is susceptible to powdery mildew.

COMMERCIAL COMPARISON

Plants of the new cultivar 'SMNPOBLR' can also be compared to the commercial variety *Physocarpus opulifo-*

*lius* 'Mindia', U.S. Plant Pat. No. 16,371. These varieties are similar in most horticultural characteristics; however 'SMNPOBLR' differs in the following:

1. Spring foliage of red/orange; whereas the 'Mindia' variety has a Spring foliage of yellow/orange.
2. Mildew resistance; whereas the variety 'Mindia' has less resistance.

BRIEF DESCRIPTION OF THE PHOTOGRAPHS

Figure 1:
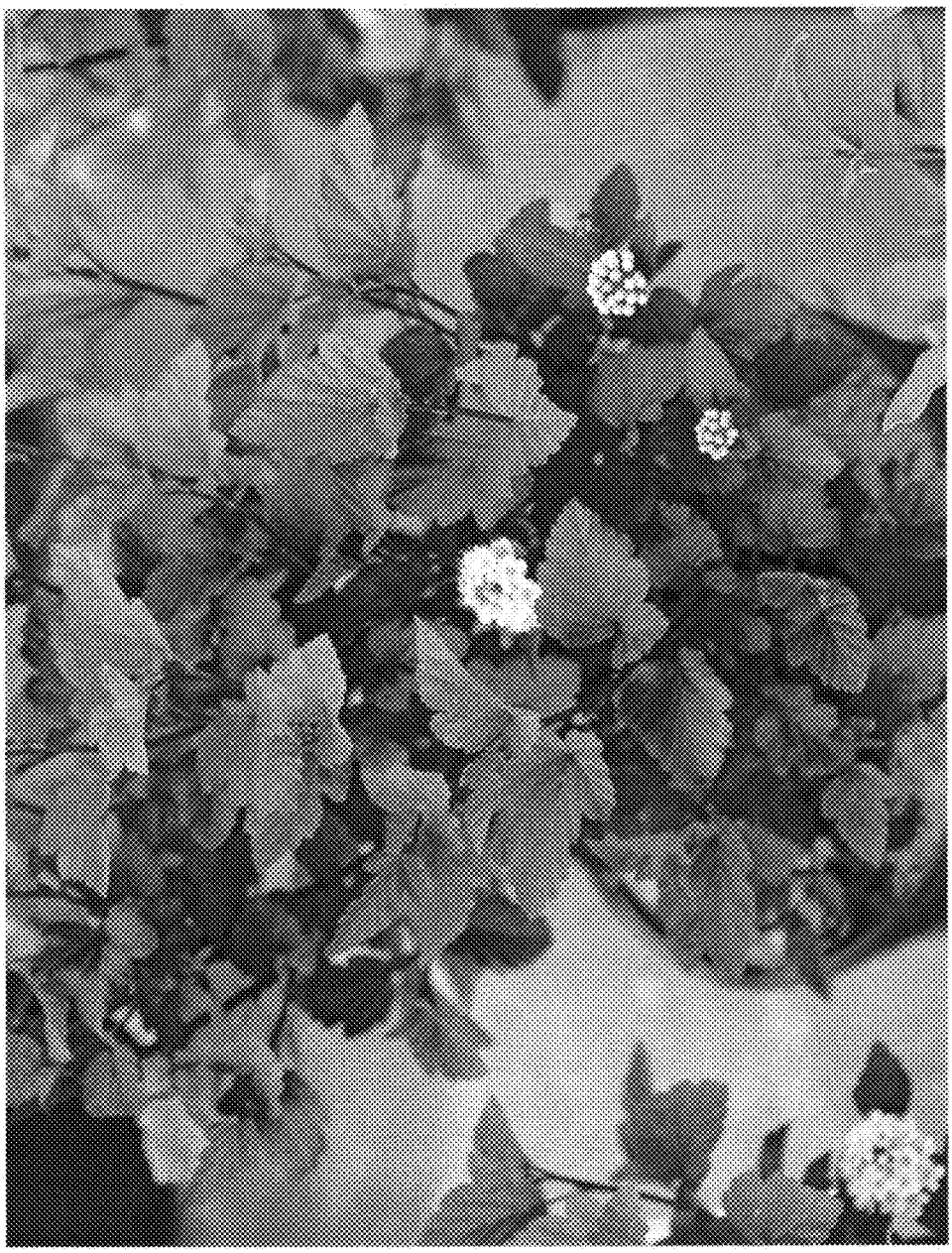

The accompanying photograph in FIG. 1 illustrates in full color a typical young plant of 'SMNPOBLR'.

Figure 2:
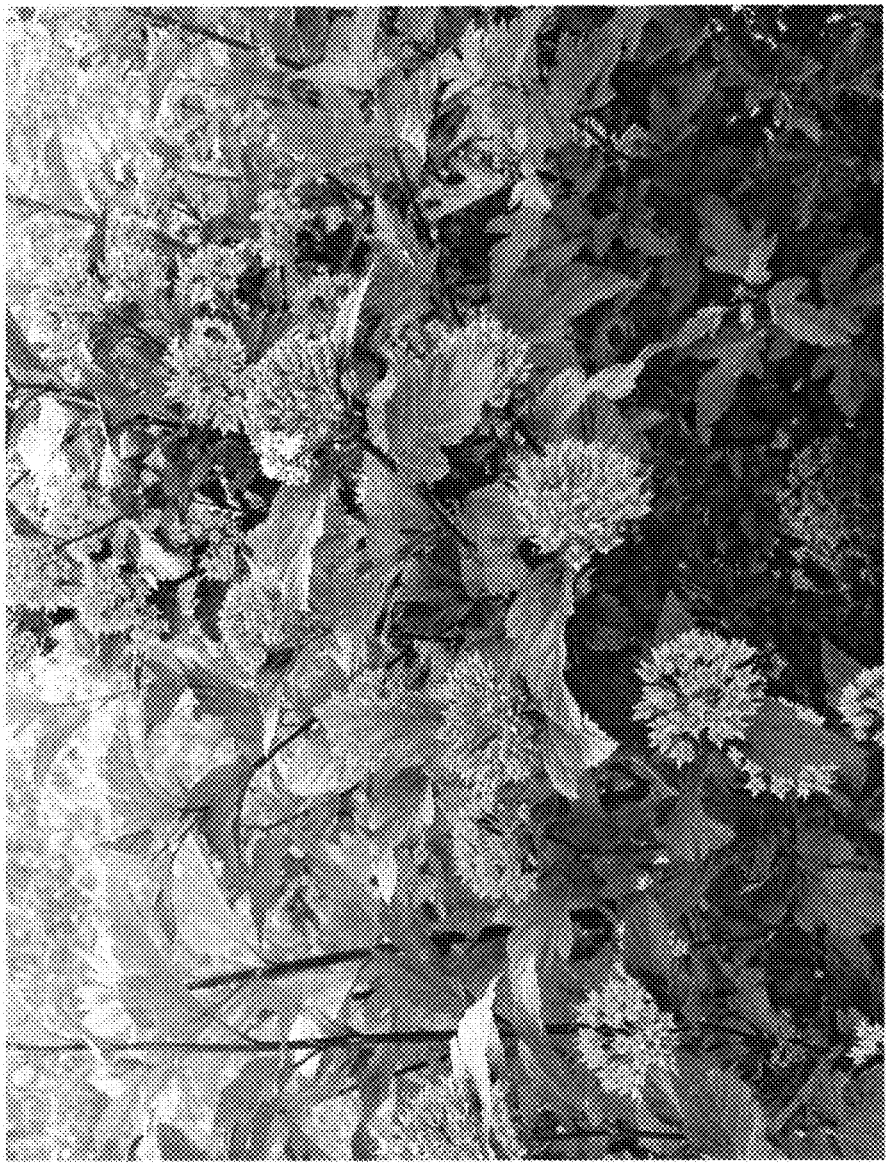

FIG. 2 illustrates in full color a typical inflorescence and foliage of 'SMNPOBLR'. The plant in FIG. 2 is in an outdoor bed with other *Physocarpus* varieties. The green foliage at the lower corner is from a different plant.

Figure 3:
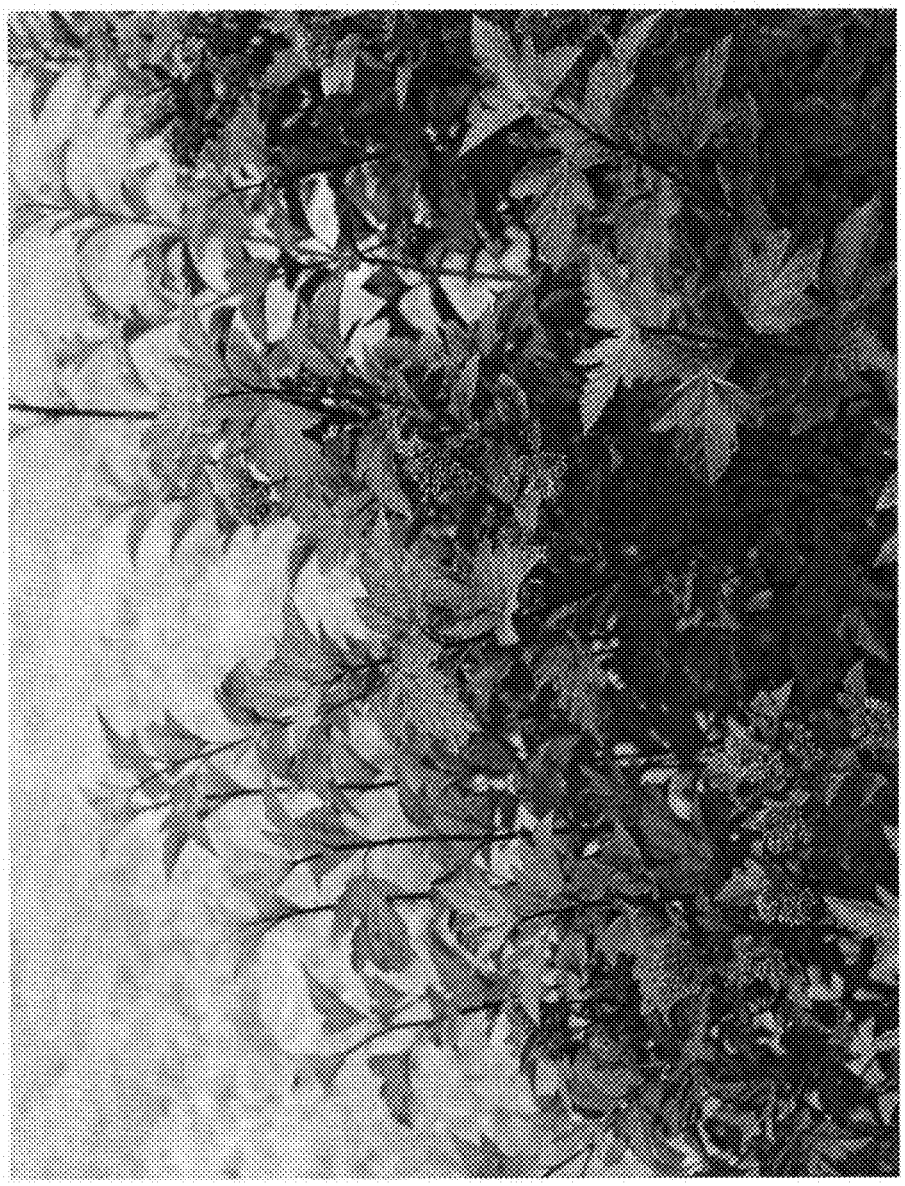

FIG. 3 illustrates in full color a typical foliage of 'SMNPOBLR', including red/orange new growth. Plants were grown outdoors in Grand Haven, Minn., in a garden setting. Age of the plant photographed is approximately 2 years from a young plant.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1995 except where general terms of ordinary dictionary significance are used. The following observations and measurements describe 'SMNPOBLR' plants grown in a polyhouse in Grand Haven, Minn. This occurred during June of 2014. The plants were approximately 2 years old grown in 2 gallon containers. The growing temperature ranged from 18° C. to 27° C. during the day, and 5° to 10° C. at night. Measurements and numerical values represent averages of typical plant types.

Botanical classification: *Physocarpus opulifolius* 'SMNPOBLR'.

PROPAGATION

Time to initiate roots: About 25 days at approximately 24° C.

Root description: Moderate to dense, fibrous and fleshy, freely branching. Colored white and brown, not accurately identified with R.H.S. chart.

Time to produce a young rooted plant: About 60 days at 24° C.

PLANT

Plant type: Shrub perennial.
Age of plant described: Approximately 2 years old.
Growth habit: Upright and rounded.
Pot size of plant described: 2 gallon pot.
Height: Approximately 60 cm to top of foliage.
Plant spread: Approximately 40 cm.
Growth rate: Moderate to fast.
Plant vigor: Good.
Branching characteristics: Free, basal branching when pinched.
Length of primary lateral branches: Approximately 35 cm.
Diameter of lateral branches: Approximately 0.5 cm.
Quantity of lateral branches: Minimum average 40.
Stem:
- *Shape*.—Square.
- *Aspect/angle*.—50° to 80°.
- *Strength*.—Good.
- *Stem color*.—Near RHS Red-Purple 59B.
- *Texture*.—Glabrous at approximately 3 to 4 years of age. Exfoliation not yet observed.

Internode length: Average 4.5 cm.

FOLIAGE

Leaf:
- *Arrangement*.—Alternate, single.
- *Average length*.—Approximately 7.0 cm.
- *Average width*.—Approximately 6.5 cm.
- *Shape of blade*.—Tri-lobed, overall Rhomboid.
- *Apex*.—Acute.
- *Base*.—Cordate.
- *Attachment*.—Stalked.
- *Margin*.—Doubly-Serrate.
- *Texture of top surface*.—Smooth.
- *Texture of bottom surface*.—Smooth.
- *Pubescence?*.—None.
- *Color*.—Young foliage upper side: Near RHS Greyed-Red 178A. Young foliage under side: Near RHS Greyed-Orange 166A. Mature foliage upper side: Near RHS Greyed-Purple 187A. Mature foliage under side: Near RHS Greyed-Purple 186B to Greyed-Green 194A. No significant Fall foliage color change.
- *Venation*.—Type: Palmate. Venation color upper side: Near RHS Green 187A. Venation color under side: Near RHS Green 194A.
- *Petiole*.—Average Length: Approximately 1.75 cm. Diameter: Approximately 0.15 cm. Petiole color upper side: Near RHS Red-Purple 60A. Petiole color lower side: Near RHS Red-Purple 60A. Petiole Texture upper side: Smooth, waxy. Petiole Texture lower side: Smooth, waxy.
- *Stipule*.—Highly reduced, less than 2 mm, insignificant.

FLOWER

Natural flowering season: April-May.
Inflorescence type and habit: Terminal corymb.
Quantity of flowers per inflorescence: About 35.
Inflorescence size:
- *Width*.—Approximately 3.0 cm.
- *Height*.—Approximately 2.75 cm.

Quantity of flowers per lateral stem: Approximately 25 (in a #3 Container).
Quantity of flowers per plant: Approximately 300 (in a #3 Container).
Individual flowers:
Flower form: Cupped/star-like.
Flower aspect: Upright.
Size:
- *Diameter*.—Approximately 0.8 cm.
- *Length*.—Approximately 1.8 cm.
- *Depth*.—Approximately 1.8 cm.
- *Persistence*.—Self-cleaning, usually turning into a seed head.

Petal:
- *Petal arrangement*.—Whorl.

*Number of petals per flower.*—5.
*Petal appearance.*—Smooth, opaque.
*Petal shape.*—Rounded, obovate.
*Margin.*—Smooth, entire.
*Tip shape.*—Rounded.
*Length.*—0.5 cm.
*Width.*—0.5 cm.
*Texture.*—Upper: Smooth. Lower: Smooth.

Petal color:
*When opening.*—Upper surface: Near RHS White 155A flushed Red-Purple 69B. Lower surface: Near RHS White 155A flushed Red-Purple 62D.
*Fully opened.*—Upper surface: Near RHS White 155A flushed Red-Purple 69B. Lower surface: Near RHS White 155A flushed Red-Purple 62D.
*Fading.*—Upper surface: Near RHS White 155A flushed Red-Purple 73D. Lower surface: Near RHS White 155A flushed Red-Purple 73D.

Bud:
*Shape.*—Round.
*Length.*—Approximately 0.2 cm.
*Diameter.*—Approximately 0.2 cm.
*Color.*—Near RHS Red-Purple 73C.

Sepals:
*Shape.*—Widely Triangular.
*Arrangement.*—Rotate.
*Length.*—Approximately 0.2 cm.
*Width.*—Approximately 0.2 cm.
*Margin.*—Entire.
*Base.*—Truncate.
*Tip.*—Acute.
*Texture.*—Smooth.
*Number of sepals.*—4.
*Color (mature).*—Upper side: Near RHS Yellow-Green 149D. Under side: Near RHS Yellow-Green 149C with Red-Purple 64B tips.

Peduncle:
*Length.*—Average 1.0 cm.
*Diameter.*—0.15 cm.
*Color.*—Near RHS Yellow-green 147C.
*Orientation.*—60°.
*Strength.*—Good.
*Texture.*—Smooth, waxy.

Pedicels:
*Length.*—0.8 to 1.0 cm.
*Diameter.*—Less than 0.1 cm.
*Angle.*—60° to 90°.
*Strength.*—Good.
*Texture.*—Smooth.
*Color.*—Near RHS Yellow-Green 153C.

REPRODUCTIVE ORGANS

Stamens:
*Number.*—20.
*Filament length.*—Approximately 0.4 to 0.5 cm.
*Filament color.*—Near RHS White 155B.

Anthers:
*Shape.*—Elliptic to round.
*Length.*—0.5 cm.
*Color.*—Near RHS Brown 200A.
*Pollen.*—Moderate.
*Pollen color.*—Near RHS Red-Purple 58A.

Pistil:
*Number.*—Average of 4.
*Length.*—Approximately 0.3 cm.
*Style.*—Length: Approximately 0.3 cm. Color: Near RHS White 155B.
*Stigma.*—Shape: Club-shaped. Color: Near RHS Yellow-Green 153D. Ovary color: Near RHS Yellow-Green 151D.

OTHER CHARACTERISTICS

Seeds and fruits: Three lobed chambers, overall 5 mm tall, 4 mm in diameter. Colored near RHS Red 42B. Seed spherical, less than 0.5 mm in diameter, colored near Orange-White 159A.

Garden performance: Good.

Disease/pest resistance: Good resistance to powdery mildew. Neither resistance nor susceptibility to pathogens and pests common to *Physocarpus* have been observed. Many Genus and species of powdery mildew are found on *Physocarpus*. The inventor cannot accurately identify which powdery mildew the new variety is resistant to.

Temperature tolerance: The new variety tolerates temperatures between −31° C. to 38° C.

What is claimed is:

1. A new and distinct cultivar of *Physocarpus* plant named 'SMNPOBLR' as herein illustrated and described.

* * * * *